(12) United States Patent
Hammon et al.

(10) Patent No.: US 7,074,955 B2
(45) Date of Patent: Jul. 11, 2006

(54) SAFE OPERATION OF A CONTINUOUS HETEROGENEOUSLY CATALYZED GAS-PHASE PARTIAL OXIDATION OF AT LEAST ONE ORGANIC COMPOUND

(75) Inventors: Ulrich Hammon, Mannheim (DE); Jochen Meschke, Otterstadt (DE); Ulrich Rauh, Frankenthal (DE); Klaus Joachim Müller-Engel, Stutensee (DE); Peter Schlemmer, Eisenberg (DE); Volker Schliephake, Schifferstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 204 days.

(21) Appl. No.: 10/459,782

(22) Filed: Jun. 12, 2003

(65) Prior Publication Data

US 2004/0015012 A1 Jan. 22, 2004

(30) Foreign Application Priority Data

Jul. 17, 2002 (DE) .......................... 102 32 482

(51) Int. Cl.
*C07C 51/16* (2006.01)

(52) U.S. Cl. ............... 562/532; 562/542; 562/545; 562/549; 568/451; 568/458; 568/459

(58) Field of Classification Search .......... 562/524, 562/526, 527, 531, 537, 538, 541, 542; 568/420, 568/431, 338
See application file for complete search history.

(56) References Cited

U.S. PATENT DOCUMENTS

| 3,119,837 | A | 1/1964 | Kingsley et al. |
|---|---|---|---|
| 3,799,886 | A | 3/1974 | Felice et al. |
| 3,956,377 | A | 5/1976 | Dolhyj et al. |
| 4,077,912 | A | 3/1978 | Dolhyj et al. |
| 4,408,079 | A | 10/1983 | Merger et al. |
| 4,496,770 | A | 1/1985 | Duembgen et al. |
| 4,870,201 | A | 9/1989 | Ramachandran et al. |
| 5,008,414 | A | 4/1991 | Ramachandran et al. |
| 5,173,468 | A | 12/1992 | Boehning et al. |
| 5,221,767 | A | 6/1993 | Boehning et al. |
| 5,231,226 | A | 7/1993 | Hammon et al. |
| 5,235,071 | A | 8/1993 | Ueda et al. |
| 5,264,625 | A | 11/1993 | Hammon et al. |
| 5,281,745 | A | 1/1994 | Ushikubo et al. |
| 5,472,925 | A | 12/1995 | Ushikubo et al. |
| 5,668,077 | A | 9/1997 | Klopries et al. |
| 5,734,068 | A | 3/1998 | Klopries et al. |
| 6,090,977 | A | 7/2000 | Hefner et al. |
| 6,252,122 | B1 | 6/2001 | Tenten et al. |
| 2002/0037488 | A1 * | 3/2002 | Hirao et al. ............. 431/268 |

FOREIGN PATENT DOCUMENTS

DE  1 254 137  11/1967

(Continued)

OTHER PUBLICATIONS

Beyer, Lehrbuch der organ. Chemie, $17^{th}$ Edition, p. 261, "Hirzel Verlag Stuttgart", 1973.

*Primary Examiner*—Johann Richter
*Assistant Examiner*—Karl Puttlitz
(74) *Attorney, Agent, or Firm*—Oblon, Spivak, McClelland, Maier & Neustadt, P.C.

(57) ABSTRACT

A continuously operated heterogeneously catalyzed gas-phase partial oxidation of at least one organic compound in an oxidation reactor is operated safely by a process in which an explosion diagram for the feed gas mixture is deposited as the basis of a cut-out mechanism in a computer.

18 Claims, 4 Drawing Sheets

FOREIGN PATENT DOCUMENTS

| | | |
|---|---|---|
| DE | 2 025 430 | 12/1971 |
| DE | 2 159 346 | 6/1972 |
| DE | 2 106 796 | 8/1972 |
| DE | 2 351 151 | 4/1974 |
| DE | 25 26 238 | 1/1976 |
| DE | 40 22 212 | 1/1992 |
| DE | 41 32 263 | 4/1993 |
| DE | 41 32 684 | 4/1993 |
| DE | 43 11 608 | 12/1994 |
| DE | 196 22 331 | 12/1997 |
| DE | 100 28 582 | 12/2001 |
| DE | 100 46 672 | 3/2002 |
| DE | 101 31 297 | 1/2003 |
| EP | 0 058 927 | 9/1982 |
| EP | 0 092 097 | 10/1983 |
| EP | 0 372 972 | 6/1990 |
| EP | 0 522 871 | 1/1993 |
| EP | 0 529 853 | 3/1993 |
| EP | 0 608 838 | 8/1994 |
| EP | 0 731 080 | 9/1996 |
| EP | 1 090 684 | 4/2001 |
| EP | 1 180 508 | 2/2002 |
| GB | 1 291 354 | 10/1972 |
| GB | 1 346 943 | 2/1974 |
| GB | 1 369 639 | 10/1974 |
| GB | 1 464 198 | 2/1977 |
| WO | WO 01/96270 | 12/2001 |
| WO | WO 01/96271 | 12/2001 |
| WO | WO 02/06199 | 1/2002 |

* cited by examiner

SAFE OPERATION OF A CONTINUOUS HETEROGENEOUSLY CATALYZED GAS-PHASE PARTIAL OXIDATION OF AT LEAST ONE ORGANIC COMPOUND

BACKGROUND OF THE INVENTION

1. Field of the Invention

The present invention relates to a process for the safe operation of a continuously operated heterogeneously catalyzed gas-phase partial oxidation of at least one organic compound in an oxidation reactor whose feed gas mixture comprises, in addition to the at least one organic compound to be partially oxidized and molecular oxygen as an oxidizing agent, at least one diluent gas substantially inert under the conditions of a heterogeneously catalyzed gas-phase partial oxidation, in which a cut-out mechanism is used for preventing the oxidation reactor from being fed with a feed gas mixture whose composition is an explosive one.

2. Description of the Related Art

Here, a complete oxidation of an organic compound with molecular oxygen is understood as meaning that the organic compound is converted under the reactive action of molecular oxygen so that all the carbon contained in the organic compound is converted into oxides of carbon and all the hydrogen contained in the organic compound is converted into oxides of hydrogen. All compounds of an organic compound under the reactive action of molecular oxygen which differ from this are summarized here as partial oxidations of an organic compound.

In particular, partial oxidations are to be understood here as meaning those reactions of organic compounds under the reactive action of molecular oxygen in which the organic compound to be partially oxidized contains at least one chemically bonded oxygen atom more after the end of the reaction than before the partial oxidation is carried out.

A diluent gas substantially inert under the conditions of the heterogeneously catalyzed gas-phase partial oxidation is understood as meaning those diluent gases whose components—each considered by itself—remain unchanged to an extent of more than 95, preferably more than 99, mol % under the conditions of the heterogeneously catalyzed gas-phase partial oxidation.

Gaseous mixtures containing molecular oxygen and a partially oxidizable gaseous organic compound are potentially explosive gas mixtures.

What is decisive with regard to answering the question as to whether the gas mixture is explosive or not is whether or not combustion (ignition, explosion) initiated by a local ignition source (e.g. glowing platinum wire) spreads in the gas mixture present under specific starting conditions (pressure, temperature) (cf. DIN 51649). If said combustion spreads, the mixture is to be defined here as being explosive. If no spread occurs, the mixture is classified as nonexplosive in this document.

The investigations required for this purpose are usually carried out in a closed stainless steel 51 high-pressure container. The gas mixture in the initially evacuated high-pressure container is usually produced by the partial pressure method. After mixing for about 10 minutes by means of a magnetic stirrer, an attempt is made to ignite the gas mixture present in each case at a specific starting pressure and a specific starting temperature by means of a melting platinum wire. Any automatic spread of a reaction front (explosion) triggered thereby is detected by the increase in the internal pressure in the container as a function of time (e.g. measurement using a piezoelectric pressure transducer) and by the increase in the temperature in the container (cf. for example EP-A 731080 and DE-A 19622331.

Gases whose mixtures with air are not capable of combustion reaction spreading from an ignition source at any mixing ratios are to be defined here as being nonflammable gases. Typical examples of nonflammable gases are $CO_2$, $H_2O$, $N_2$ and all noble gases.

Gases whose mixtures with air are capable of a combustion reaction spreading from an ignition source at specific mixing ratios are to be defined here as being flammable gases. Examples of flammable gases are hydrogen, ethane, propane, butane and diethyl ether.

While nonflammable gases are inert diluent gases suitable in principle for heterogeneously catalyzed gas-phase partial oxidations of organic compounds, in the case of flammable gases this must be determined by a person skilled in the art with respect to a specific heterogeneously catalyzed gas-phase partial oxidation by means of a few preliminary experiments.

It is generally known that numerous key chemicals can be produced by partial and heterogeneously catalyzed oxidation of various organic compounds with molecular oxygen in the gas phase. Examples are the reaction of propylene to give acrolein and/or acrylic acid (cf. for example DE-A 2351151), the reaction of tert-butanol, isobutene, isobutane, isobutyraldehyde or the methyl ether of tert-butanol to give methacrolein and/or methacrylic acid (cf. for example DE-A 2526238, EP-A 92097, EP-A 58927, DE-A 4132263, DE-A 4132684 and DE-A 4022212), the reaction of acrolein to give acrylic acid, the reaction of methacrolein to give methacrylic acid (cf. for example DE-A 2526238), the reaction of o-xylene or naphthalene to give phthalic anhydride (cf. for example EP-A 522871) and the reaction of butadiene to give maleic anhydride (cf. for example DE-A 2106796 and DE-A 1624921), the reaction of n-butane to give maleic anhydride (cf. for example GB-A 1464198 and GB-A 1291354), the reaction of indanes to give, for example, anthraquinone (cf. for example DE-A 2025430), the reaction of ethylene to give ethylene oxide or of propylene to give propylene oxide (cf. for example DE-B 1254137, DE-A 2159346, EP-A 372972, WO 89/0710, DE-A 4311608 and Beyer, Lehrbuch der organischen Chemie, 17th edition (1973), Hirzel Verlag Stuttgart, page 261), the reaction of propylene and/or acrolein to give acrylonitrile (cf. for example DE-A 2351151), the reaction of isobutene and/or methacrolein to give methacrylonitrile (i.e. the term partial oxidation is intended in this document also to include partial ammoxidation, i.e. partial oxidation in the presence of ammonia), the oxidative dehydrogenation of hydrocarbons (cf. for example DE-A 2351151), the reaction of propane to give acrylonitrile or to give acrolein and/or acrylic acid (cf. for example DE-A 10131297, EP-A 1090684, EP-A 608838, DE-A 10046672, EP-A 529853, WO 01/96270 and DE-A 10028582) etc.

The catalysts to be used are usually solids.

The catalysts used are particularly frequently oxide materials or noble metals (e.g. Ag). Apart from oxygen, the catalytically active oxide material may contain only one other element or more than one other element (multielement oxide materials). Particularly frequently used catalytically active oxide materials are those which comprise more than one metallic, in particular transition metal, element. In this case, the term multimetal oxide materials is used. Usually, multielement oxide materials are not simple physical mixtures of oxides of the elemental constituents but heterogeneous mixtures of complex polycompounds of these elements.

In general, heterogeneously catalyzed gas-phase partial oxidations, in particular the abovementioned ones, are carried out at elevated temperatures (as a rule a few hundred degrees C., usually from 100 to 600° C.).

Since most heterogeneously catalyzed gas-phase partial oxidations are strongly exothermic, they are, for reasons relating to heat removal, expediently often carried out in a fluidized bed or in fixed-bed reactors comprising a multiplicity of catalyst tubes, a heat exchange medium being passed through the space surrounding the catalyst tubes in said reactors.

The operating pressure (absolute pressure) in heterogeneously catalyzed gas-phase partial oxidations may be either below, at or above 1 atm. As a rule, it is from 1 to 10, generally from 1 to 3, atm. The desired reaction takes place during the residence time of the reaction gas mixture in the catalyst bed through which it is passed.

Owing to the generally pronounced exothermic character of most heterogeneously catalyzed gas-phase partial oxidations of organic compounds with molecular oxygen, the reactants are usually diluted with a gas which is substantially inert under the conditions of the gas-phase catalytic partial oxidation and, with its heat capacity, is capable of absorbing liberated heat of reaction.

One of the most frequently used inert diluent gases is molecular nitrogen, which is automatically used whenever air is used as an oxygen source for the heterogeneously catalyzed gas-phase partial oxidation.

Another inert diluent gas often used is steam, owing to its general availability. Moreover, both nitrogen and steam advantageously form nonflammable inert diluent gases.

Often recycle gas is also concomitantly used as inert diluent gas (cf. for example EP-A 1180508). Recycle gas is defined as the residual gas which remains after a one-stage or multistage (in the multistage heterogeneously catalyzed gas-phase partial oxidation of organic compounds, the gas-phase partial oxidation, in contrast to the one-stage heterogeneously catalyzed gas-phase partial oxidation, is carried out not in one reactor but in at least two reactors connected in series, as a rule oxidizing agent being added between successive reactors; multiple stages are used in particular when the partial oxidation is carried out in successive steps; in these cases, it is frequently expedient to adapt both the catalyst and the other reaction conditions in an optimum manner to the respective reaction step and to carry out the reaction step in a separate reactor, in a separate reaction stage; however, multiple stages may also be used when, for reasons relating to heat removal or for other reasons (cf. for example DE-A 19902562), the reaction is spread over a plurality of reactors connected in series; an example of a heterogeneously catalyzed gas-phase partial oxidation frequently carried out in two stages is the partial oxidation of propylene to acrylic acid; the propylene is oxidized to acrolein in the first reaction stage, and the acrolein to acrylic acid in the second reaction stage; in a corresponding manner, the preparation of methacrylic acid is also frequently carried out in two stages, in general starting from isobutene; both abovementioned partial oxidations can, however, also be carried out in one stage (both steps in one reactor) when suitable catalyst loads are used) heterogeneously catalyzed gas-phase partial oxidation of at least one organic compound when the desired product has been isolated more or less selectively (for example by absorption in a suitable solvent) from the product gas mixture. As a rule, it predominantly comprises the inert diluent gases used for the partial oxidation and steam usually formed as a byproduct in the partial oxidation and carbon oxides and steam formed by undesired complete oxidation. In some cases, it also contains small amounts of oxygen not consumed in the partial oxidation (residual oxygen) and/or of unconverted organic starting compounds.

The steam formed as a byproduct ensures in most cases that the partial oxidation takes place without significant volume changes of the reaction gas mixture.

According to the above, in most heterogeneously catalyzed gas-phase partial oxidations of organic compounds the inert diluent gas concomitantly used comprises $\geq 90$, frequently $\geq 95$, % by volume of $N_2$, $H_2O$, and/or $CO_2$ and thus substantially comprises nonflammable inert diluent gases.

However, the inert diluent gases concomitantly used not only ensure, in combination with the other measures used for removing the heat of reaction (e.g. external cooling), a substantially uniform temperature of the reaction gas mixture along the reaction path but also permit the safe operation of a continuous heterogeneously catalyzed gas-phase partial oxidation of organic compounds.

Figure 1:
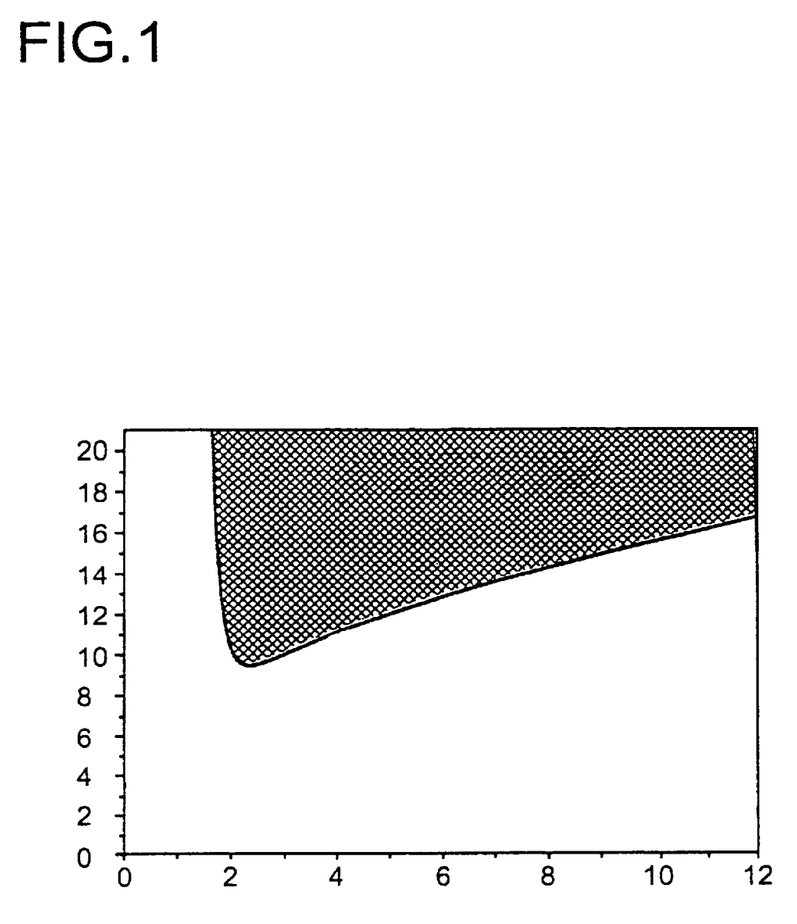
FIG. 1 shows an explosion diagram for a propylene/oxygen-nitrogen gas mixture.

If in fact the explosion behavior of a gas mixture consisting of molecular oxygen, a nonflammable inert diluent gas and a flammable organic compound and present at a specific temperature and a specific pressure is investigated as a function of the composition of the mixture, a result is obtained as shown for a typical case by the explosion diagram of FIG. 1 for the propylene/oxygen-nitrogen gas mixture.

The abscissa shows the proportion of propylene in the mixture in % by volume ($V_{C3}$), the ordinate shows the proportion of molecular oxygen in the mixture in % by volume ($V_{O2}$) and the residual amount to 100% by volume is always the molecular nitrogen.

If the composition of the gas mixture is in the hatched area of FIG. 1, it is explosive; if it is outside, it is nonexplosive. The solid line separates the explosive area from the nonexplosive area and is defined as the explosion limit.

If, for example, steam or a mixture of nitrogen and steam were to be used instead of nitrogen as the inert diluent gas, the explosion limit would be virtually coincident. This also applies to most other nonflammable inert diluent gases, as long as their specific molar heat does not differ considerably from that of molecular nitrogen. The pressure and temperature dependence of an explosion diagram is limited and, where changes are not too large, can be neglected.

If the propylene were to be replaced by a mixture of organic compounds of a specific composition or by another organic compound, the qualitative curve of the explosion limit in the explosion diagram would be qualitatively the same.

DETAILED DESCRIPTION OF THE INVENTION

It is advantageous for the present invention if the reaction gas starting mixture (the feed gas mixture) is outside the explosive area and if usually all reaction gas mixtures along the reaction path of the heterogeneously catalyzed gas-phase partial oxidation are outside the explosive area. This is because, on the one hand, pressure and temperature along the reaction path vary only to a comparatively limited extent and, on the other hand, the partial oxidation product (in this case, for example, acrolein) has an explosion diagram substantially comparable to that of the starting compound itself, owing to its similarity to the starting compound (in this case propylene). In addition, the percentage oxygen content increases along the reaction path on the way from the starting compound to the desired product, on the one hand because of its consumption and on the other hand frequently because of additional dilution due to the water of oxidation formed as a byproduct. Moreover, combustions (explosions) are free radical chain reactions. The catalysts used, with their large surface area, act as free radical scavengers in this respect.

This means that, in most continuously operated heterogeneously catalyzed gas-phase partial oxidations of at least one organic compound in an oxidation reactor, operation with a high level of safety is ensured when the composition of the reaction gas starting mixture during the continuous operation (in particular in the steady state) is always outside the explosion area at a pressure and temperature typical for the partial oxidation.

It is true that operation with a reaction gas starting mixture whose composition is inside the explosion area is also possible in principle. However, in this case, any local ignition source (for example local overheating or sparking in the reactor) can lead to an undesired explosion, which would have to be counteracted by expensive safety means (for example bursting disks, safety valves, flashback arresters) and pressure-resistant reactors, which are comparatively expensive and also complicated to maintain. In the case of toxic main products and byproducts, however, even the abovementioned countermeasures would not be sufficient.

What is important for continuous operation of a heterogeneously catalyzed gas-phase partial oxidation of at least one organic compound in an oxidation reactor with compositions of the reaction gas starting mixture which are outside the explosion area is, however, that the continuous operation has a cut-out mechanism which prevents that composition of the reaction gas starting mixture (feed gas mixture) which is outside the explosion area from migrating into the explosion area during the continuous operation (i.e. in particular in the steady state) as a result of accidental faults in the gas streams fed to the reactor for the formation of the feed gas mixture (said gas streams generally consist of air, the substance to be oxidized and inert diluent gas and/or, if required, recycle gas).

A particularly simple cut-out mechanism consists in always keeping the content of the at least one organic compound to be partially oxidized in the feed gas mixture below the limiting concentration of said compound. The content of the at least one organic compound to be partially oxidized in the feed gas mixture is below the limiting concentration when, at a predetermined content of the at least one organic compound to be partially oxidized in the feed gas mixture, the composition of the feed gas mixture (at predetermined pressure and temperature) is always outside the explosion area, independently of the quantitative composition of its other components ($O_2$/inert diluent gas).

In FIG. 1, the limiting propylene concentration is about 2% by volume (cf. also EP-B 1180508, page 8, line 32).

This means that, if the propylene concentration of the feed gas mixture is kept below 2% by volume in the heterogeneously catalyzed partial oxidation of propylene to acrolein and/or acrylic acid with the use of $N_2$ and/or steam as an inert gas, the feed gas mixture is outside the explosion area independently of the composition of the remaining >98% by volume of the feed gas mixture comprising $O_2$, $N_2$ and $H_2O$.

In the abovementioned case, monitoring the propylene concentration in the feed gas mixture as a function of time is sufficient as a cut-out mechanism. If said concentration approaches the 2% by volume limit, the propylene feed is cut off for safety reasons.

The disadvantage of this safety concept is that the space-time yield achievable thereby is itself a comparatively limited one owing to the limitation of the propene concentration in the feed gas mixture and is unsatisfactory.

As an improvement, EP-B 1180508 recommends carrying out the steady-state continuous operation of a heterogeneously catalyzed gas-phase partial oxidation of at least one organic compound in an oxidation reactor (with propene oxidation to acrolein and/or acrylic acid as an example) in such a way that the content of molecular oxygen in the feed gas mixture is always below the limiting oxygen concentration (page 8, lines 28 to 34, of EP-A 1180508). This is also recommended by EP-A 731080, on page 3, lines 29/30.

The $O_2$ content of the feed gas mixture is below the limiting oxygen concentration when, at a predetermined $O_2$ content of the feed gas mixture, the composition of the feed gas mixture (at predetermined pressure and temperature) is always outside the explosion area independently of the quantitative composition of its other components (at least one organic compound to be partially oxidized/inert diluent gas).

In FIG. 1 (which relates to 250° C. and 1 atm), the limiting oxygen concentration is about 10% by volume (cf. also EP-B 1180508, page 8, line 32).

This means that, if the oxygen concentration of the feed gas mixture is kept below 10% by volume in the heterogeneously catalyzed partial oxidation of propylene to acrolein and/or acrylic acid with the use of $N_2$ and/or steam as an inert gas, the feed gas mixture is outside the explosion area independently of the composition of the remaining >90% by volume of the feed gas mixture comprising propylene and/or $N_2/H_2O$.

Figure 2:
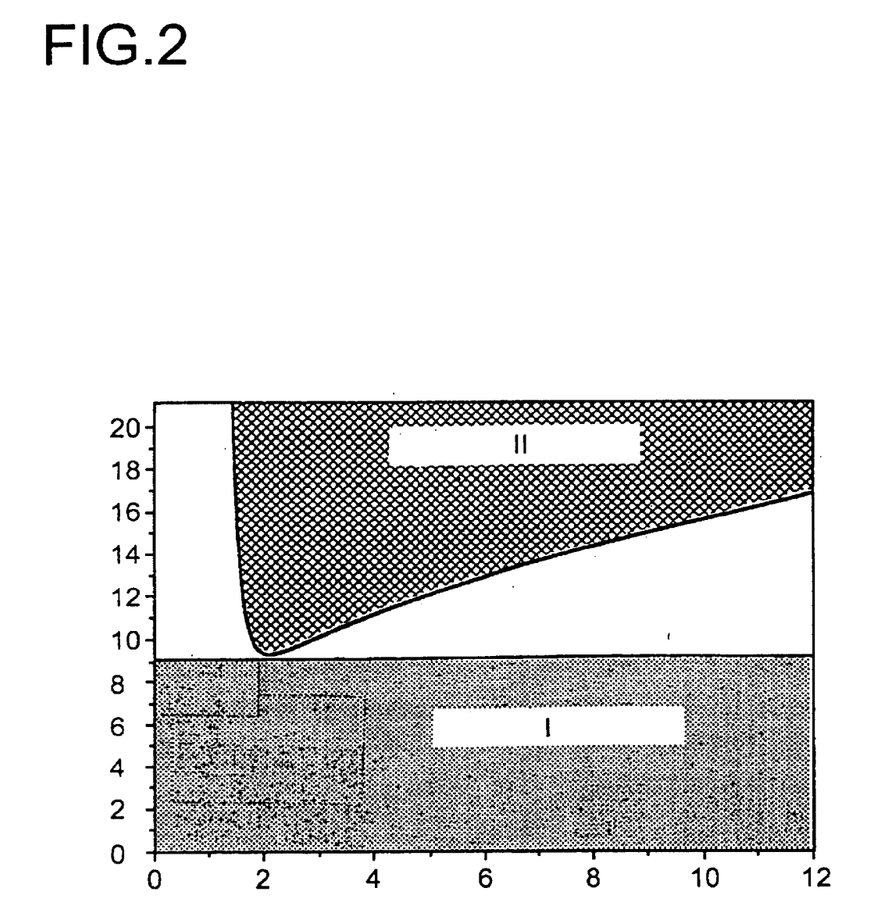
FIG. 2 shows an explosion diagram for propylene/oxygen-nitrogen gas mixture with a non-explosive region below the minimum oxygen concentration I.

Thus, the entire area I in FIG. 2 is available as an operating area in which operation is possible with a high level of safety. The area II in FIG. 2 is the explosive area, the abscissa corresponding to the propylene content in % by volume and the ordinate to the oxygen content in % by volume. The remaining amount to 100% by volume is inert diluent gas comprising $N_2$ and/or $H_2O$.

In the abovementioned case, monitoring the oxygen concentration in the feed gas mixture as a function of time is sufficient as a cut-out mechanism. If said concentration approaches the 10% by volume limit, the oxygen feed is cut off for safety reasons.

The disadvantage of this safety concept is that, on the one hand with regard to the stoichiometry of the desired partial oxidation to the desired compound but also for other reasons, it is as a rule necessary to employ the molecular oxygen used as oxidizing agent in at least stoichiometric or in superstoichiometric amounts (for example because of the reoxidation of the oxidic material used as a catalyst and for reducing carbon deposits on the catalyst).

Limitation of the oxygen concentration in the feed gas mixture is therefore inevitably also associated with a significant limitation of the space-time yield.

It is an object of the present invention to provide a process for the safe operation of a continuously operated heterogeneously catalyzed gas-phase partial oxidation of at least one organic compound (in particular all those cited at the outset) in an oxidation reactor whose feed gas mixture comprises, in addition to the at least one organic compound to be partially oxidized and molecular oxygen as oxidizing agent, at least one diluent gas substantially inert under the conditions of the heterogeneously catalyzed gas-phase partial oxidation, which process comprises a cut-out mechanism which prevents, in a manner improved compared with the prior art, the oxidation reactor from being fed with a feed gas mixture whose composition is an explosive one and, for example, permits operation with feed gases whose composition is in the white area located between the lower edge of the area II and the upper edge of the area I in FIG. 2.

In this context, consideration was also given, inter alia, to cut-out mechanisms which are based on more than only one limiting quantity to be maintained. For example, it is possible in principle to provide cut-out limits for the following quantities in a heterogeneously catalyzed gas-phase partial oxidation of propylene to acrolein and/or acrylic acid (with a propylene conversion of $\geq 95$ mol % and a selectivity of the formation of desired product of $\geq 90$ mol %), in which propylene (crude propylene) as raw material, air as an oxygen source and recycle gas as an additional inert gas source are fed to the oxidation reactor for the production of the feed gas mixture:
a) the maximum amount of air to be fed to the reactor per unit time $(V_A)_i$;
b) the maximum ratio of the amount of air fed to the reactor per unit time to the amount of propylene fed to the reactor per unit time $(Z_{A/P})$;
c) the minimum amount of recycle gas to be fed to the reactor per unit time $(V_{Re})$; and
d) the maximum concentration of the residual oxygen content in the recycle gas $(C_{O2})$.

If one of the four limits is approached (the distance should always as far as possible be $\geq 10\%$, based on the limit), the air supply is shut off for safety reasons. As a rule, the propylene supply, too, is stopped with a time lag. The operating area accessible thereby with greater operational safety is shown in FIG. 3 (the meaning of the axes and the numerical symbols are as in FIG. 2).

Figure 3:
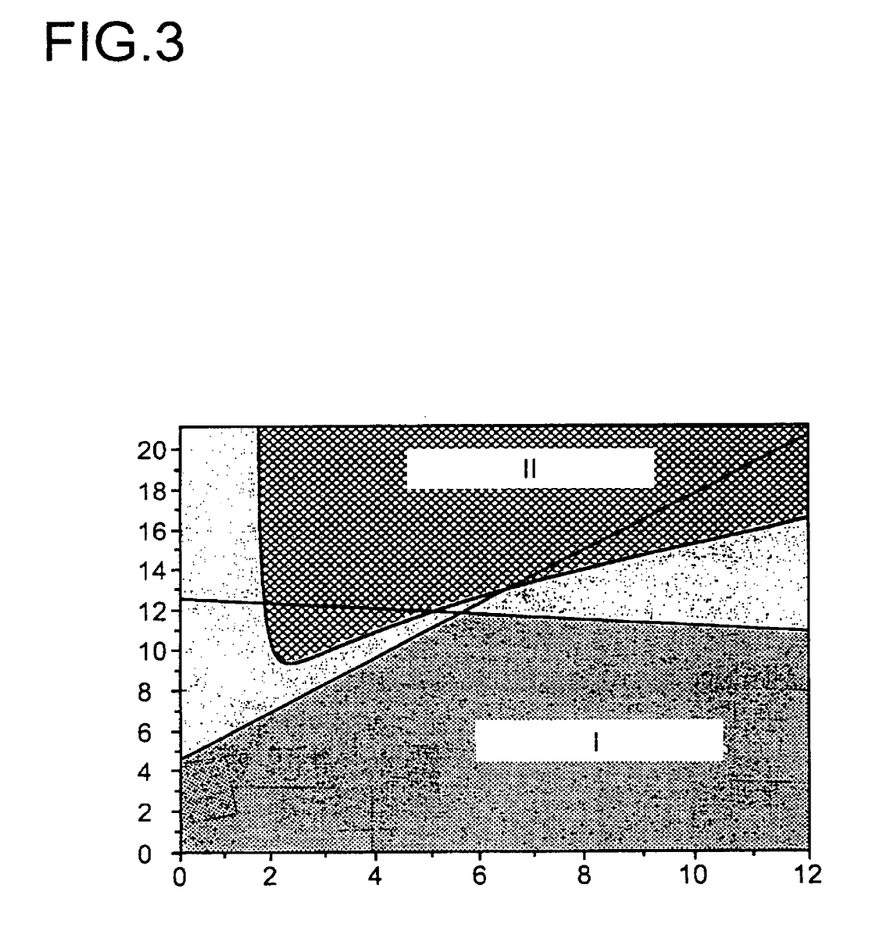
FIG. 3 shows an explosion diagram for a propylene/oxygen-nitrogen gas mixture having a non-explosive region I that is greater than the minimum limiting oxygen concentration.

The less steep straight line in FIG. 3 satisfies the equation:

$$V_{O2} = (1 - V_{C3}) \cdot \frac{A}{B},$$

with $A = C_{O2} \cdot V_{Re} + 0.21 \cdot V_A$
and $B = V_A + V_{Re}$.
The steep straight line in FIG. 3 satisfies the equation:

$$V_{O2} = C_{O2} + V_{C3}(Z_{A/P} \cdot (0.21 - C_{O2}) - C_{O2}).$$

If the cut-out limits are not exceeded, the feed gas mixture cannot leave either of the two straight lines toward higher $V_{O2}$ values, so that the hatched area characterized by I in FIG. 3 remains as an operating area. Although it comprises a small area in which the oxygen content of the feed gas mixture is above the limiting oxygen concentration, its extent is not entirely satisfactory.

we have found that this object is achieved by a process for the operation of a continuously operated heterogeneously catalyzed gas-phase partial oxidation of at least one organic compound with a high level of safety in an oxidation reactor whose feed gas mixture comprises, in addition to the at least one organic compound to be partially oxidized and molecular oxygen as an oxidizing agent, at least one diluent gas substantially inert under the conditions of the heterogeneously catalyzed gas-phase partial oxidation, in which a cut-out mechanism is used to prevent the oxidation reactor from being fed with a feed gas mixture whose composition is an explosive one, wherein the cut-out mechanism is designed as follows:
a) an explosion diagram (e.g. FIG. 1) which is characteristic of the feed gas mixture and in which a distinction is made between explosive and nonexplosive compositions as a function of the composition of the feed gas mixture is deposited in a computer;
b) a data record is established by determination with respect to the amount and, if required, composition of the gas streams fed to the reactor for producing the feed gas mixture, and is transmitted to the computer;
c) the computer calculates an actual operating point of the feed gas mixture in the explosion diagram from the data record obtained under b);
d) if the distance from the operating point to the nearest explosion limit is below a predetermined minimum value, the feed of gas streams to the reactor is automatically stopped.

The minimum value is preferably calculated from a statistical consideration of the errors of the measured quantities required for calculating the operating point.

The novel process makes it possible for the first time to carry out heterogeneously catalyzed gas-phase partial oxidations of at least one organic compound with a high level of safety and oxygen contents of the feed gas mixture which are $\geq 0.5$ or $\geq 0.75$ or $\geq 1$ or $\geq 2$ or $\geq 3$ or $\geq 5$ or $\geq 10$ percent by volume above the limiting oxygen concentration. As described above, the limiting oxygen concentration is understood as meaning that percentage volume of molecular oxygen of the feed gas mixture below which, independently of the quantity of the volume fractions of the other components of the feed gas mixture, i.e. in particular of the organic compound to be partially oxidized and the inert diluent gas, a combustion (explosion) initiated by a local ignition source (e.g. local overheating or sparking in the reactor) is no longer capable, at a given pressure and temperature of the feed gas mixture (reference values should be the temperature and pressure of the feed gas mixture on entry into the catalyst bed), of spreading in said feed gas mixture from the ignition source.

For safety reasons, it may be expedient to deposit in the computer as an explosion diagram not the curve of the experimentally determined explosion limit but a switching curve shifted downward relative to this by a safety margin. The safety margin is expediently chosen so that all sources of error and inaccuracies of measurement which are included in the determination of the operating point of the feed gas mixture are thus taken into account. The safety margin can be determined both by a consideration of absolute error and by a statistical consideration of errors. As a rule, a safety margin of from 0.1 to 0.4% by volume of $O_2$ is sufficient.

The term reactor is intended here to include not laboratory reactors but only reactors on an industrial scale, since laboratory reactors are subject to different safety requirements in practice. Accordingly, the reactors affected here should have an annual output (based on 8000 operating hours per year) of at least 2000 metric tons of desired products.

This means that, in the case of catalyst tube-bundle reactors, the number of catalyst tubes of reactors referred to in this document is as a rule from 500 to 50000, frequently from 10000 to 30000.

The novel process is suitable in principle for all heterogeneously catalyzed partial oxidations mentioned specifically at the beginning of this document.

However, it is suitable in particular for the heterogeneously catalyzed partial oxidation of propylene to acrolein and/or acrylic acid which is carried out in one stage in the tube-bundle reactor, and for the first stage of a heterogeneously catalyzed partial oxidation of propylene to acrolein and/or acrylic acid which is carried out in a plurality of stages in tube-bundle reactors, as described in EP-A 700893, EP-A 700714, DE-A 19910508 and DE-A 19919596.

Instead of pure propylene, crude propene which also contains larger or smaller amounts of other organic compounds in addition to propylene is as a rule used as raw material for this process. This crude propene may be, for example, crude propene obtained from naphtha crackers or from dehydrogenations and may have, for example, the following specifications:

a) polymer-grade propylene:
  $\leq 99.6\%$ by weight of propene
  $\leq 0.4\%$ by weight of propane,
  $\leq 300$ ppm by weight of ethane and/or methane,
  $\leq 5$ ppm by weight of $C_4$-hydrocarbons,
  $\leq 1$ ppm by weight of acetylene,
  $\leq 7$ ppm by weight of ethylene,
  $\leq 5$ ppm by weight of water,
  $\leq 2$ by weight of $O_2$,
  $\leq 2$ ppm by weight of sulfur-containing compounds (calculated as sulfur),
  $\leq 1$ ppm by weight of chlorine-containing compounds (calculated as chlorine),
  $\geq 5$ ppm by weight of $CO_2$,
  $\leq 5$ ppm by weight of CO,
  $\leq 10$ ppm by weight of cyclopropane,
  $\leq 5$ ppm by weight of propadiene and/or propyne,
  $\leq 10$ ppm by weight of $C_{\geq 5}$-hydrocarbons and
  $\leq 10$ ppm by weight of carbonyl-containing compounds (calculated as $Ni(CO)_4$);

b) chemical-grade propylene:
  $\geq 93\%$ by weight of propene,
  $\leq 7\%$ by weight or propane,
  $\leq 0.2\%$ by weight of methane and/or ethane,
  $\leq 5$ ppm by weight of ethylene,
  $\leq 20$ ppm by weight of propadiene and/or propyne,
  $\leq 100$ ppm by weight of cyclopropane,
  $\leq 50$ ppm by weight of butene,
  $\leq 50$ ppm by weight of butadiene,
  $\leq 200$ ppm by weight of $C_4$-hydrocarbons,
  $\leq 10$ ppm by weight of $C_{\geq 5}$-hydrocarbons,
  $\leq 2$ ppm by weight of sulfur-containing compounds (calculated as sulfur),
  $\leq 0.1$ ppm by weight of sulfides (calculated as $H_2S$),
  $\leq 1$ ppm by weight of chlorine-containing compounds (calculated as chlorine),
  $\leq 1$ ppm by weight of chlorides (calculated as $Cl^{\ominus}$) and
  $\leq 30$ ppm by weight of water.

Since propane is as a rule an inert gas for the purposes of the heterogeneously catalyzed partial oxidation of propylene, the propane content in the crude propylene can however also be higher.

It is expedient to use air (i.e. a mixture which substantially comprises 21% by volume of molecular oxygen and 79% by volume of molecular nitrogen) as an oxygen source for the process under discussion. The molecular nitrogen accompanying the molecular oxygen in air automatically forms diluent gas. As a rule, steam and/or recycle gas is concomitantly used as further diluent gas.

With the catalysts and working-up processes customary in the prior art (cf. EP-A 700714, DE-A 19910508, EP-A 700893, DE-A 19910506, EP-A 982287, EP-A 982289, DE-A 19924532, DE-A 10115277, EP-A 982288), the recycle gas typically has the following compositions:
3–5% by volume of molecular oxygen,
1–5% by volume of steam,
0–3% by volume of carbon monoxide,
0–8% by volume of carbon dioxide,
0–2% by volume of propane,
0.1–0.5% by volume of propylene and
85–95% by volume of molecular nitrogen.

Since the explosion behavior of propane and propylene is comparable and steam and nitrogen affect the explosion diagram of propane and/or propene in a scarcely distinguishable manner, for example, the following are suitable as a characteristic explosion diagram to be deposited according to the invention in the computer:

a) the propylene/$O_2$—$N_2$ diagram;
b) the propane/$O_2$—$N_2$ diagram;
c) the propylene/$O_2$—$H_2O$ diagram;
d) the propane/$O_2$—$H_2O$ diagram;
e) the propylene/$O_2$—($N_2$/$H_2O$) diagram;
f) the propane/$O_2$—($N_2$/$H_2O$) diagram.

According to the invention, the crude propene/$O_2$—$N_2$ explosion diagram is preferably deposited in the computer.

The temperature chosen for the experimental determination of the explosion diagram is a temperature which is not too far away from the temperature range which is covered by the partial oxidation. Depending on the catalyst used, these reaction temperatures may be from 300 to 400° C. (a temperature increase of 100° C. shifts the explosion limit downward by about 10%). The temperature of the feed gas mixture on entry into the catalyst bed is preferably chosen. The entry pressure in the case of the partial oxidation under discussion is usually from 1 to 5 bar. Since the effect of the pressure on the curve of the explosion limit is comparatively not very pronounced, the explosion diagram to be deposited according to the invention can, for the sake of simplicity, be determined at 1 bar. However, the pressure on entry into the oxidation reactor is preferably chosen.

Air, crude propene and recycle gas and/or steam are fed to the relevant oxidation reactor usually in such a way that they arrive from separate lines and are first fed to a mixer, for example a static mixer (chamber with internals which generate turbulence), in which they are homogeneously mixed and then, if necessary after heating to the inlet temperature, fed to the oxidation reactor (the entry of the individual gases into the line leading to the static mixer is expediently in the sequence recycle gas and/or steam, crude propene, air).

In order to calculate a useful actual operating point of the feed gas mixture in the explosion diagram, for example, the experimental determination of the following measured quantities is sufficient:

a) the amount of air in $m^3$(S.T.P.) fed to the mixer per unit time;
b) the amount of crude propene in $m^3$(S.T.P.) fed to the mixer per unit time;

c) the amount of steam and/or recycle gas in m³(S.T.P.) fed to the mixer per unit time;
d) the $O_2$ content of the recycle gas.

The oxygen and nitrogen content of the air is known, the amount of crude propene and the amount of any steam concomitantly used are obtained as a direct result of the measurement, and the recycle gas is assumed to consist exclusively of nitrogen, apart from its oxygen content. If the recycle gas is also to contain flammable components, these are not disadvantageous with regard to safety since their presence in the explosion diagram would merely mean a shift of the real operating point to the right relative to the calculated operating point. Steam contained in small amounts in the recycle gas or carbon oxides present can be evaluated as nitrogen with regard to relevance to safety.

The quantitative measurement of the gas streams fed to the reactor can be carried out using any measuring apparatus suitable for this purpose. Examples of suitable measuring apparatuses of this type are all flow meters, such as throttle apparatuses (for example apertures or Venturi tubes), displacement flow meters, float-tight flow meters, turbine flow meters, ultrasonic flow meters, vortex precession flow meters and mass flow meters. Venturi tubes are preferred according to the invention because of the small pressure drop. By taking into account pressure and temperature, the measured volume flow rates can be converted into m³(S.T.P.).

The determination of the oxygen content in the recycle gas can be carried out, for example, in-line as described in DE-A 10117678. However, it can in principle also be carried out on-line by taking a sample of the product gas mixture arriving from the partial oxidation before its entry into the desired product isolation (working-up) and analyzing said sample on-line so that the analysis is effected in a period which is shorter than the residence time of the product gas mixture in the working-up. This means that the amount of gas to the analyzer must be chosen to be appropriately large via an analysis gas bypass and the pipeline system to the analyzer must be chosen to be appropriately small. Of course, it would also be possible to carry out an $O_2$ determination in the feed gas instead of the recycle gas analysis. It is of course also possible to carry out both procedures. The determination of the operating point for application of the novel safety programmable logic control (SPLC) is expediently composed of at least three channels.

This means that each quantitative measurement is carried out by means of three fluid flow indicators (FFI) connected in series or in parallel. The same applies to the $O_2$ analysis. If one of the three operating points of the feed gas mixture in the explosion diagram which were calculated from the three data records falls below the predetermined minimum margin, the gas feed is automatically closed, for example in the sequence air, after a time lag propene and finally any steam and/or recycle gas.

From the point of view of subsequent restarting, it may be expedient to continue circulating steam and/or recycle gas.

Alternatively, it is also possible to calculate a mean operating point in the explosion diagram from the three individual measurements. If its distance from the explosion limit falls below a minimum value, automatic shut-off is effected as described above.

A typical steady-state operating point of the novel process may be, for example, as follows (all amounts in m³(S.T.P.)):

Air:polymer-grade propylene:recycle gas:steam= 6.9:1:8.5:0, the recycle gas having the following composition:

| Component | % by volume |
| --- | --- |
| Oxygen | 3.3 |
| Water | 1.5 |
| Carbon monoxide | 0.8 |
| Carbon dioxide | 1.6 |
| Propane | 0.3 |
| Propene | 0.3 |
| Acrolein | 0.05 |
| Nitrogen | 92.15 | or =64.8:7.6:2.5:8.5,
or =64:6:0:34.

In principle, the novel process can be used not only for steady-state operation but also for startup and shutdown of the partial oxidation.

However, very exact and reliable measurements are required for calculating the operating points of the feed gas mixture from the measured values for the individual flow rates.

Since from the point of view of application technology, however, small amounts of gas compared with the amounts for which the production plant is designed are used for starting a heterogeneously catalyzed gas-phase partial oxidation, and the measured values of flow meters are comparatively unreliable particularly in the first third of their measuring range, as a rule the following procedure is adopted when starting the partial oxidation:

Opening of the feed of first air and then propene is enabled only when the feed rate of the diluent gas (steam and/or recycle gas) has increased to a minimum value which is, for example, 70% of the maximum possible air feed rate. In this way, propene and air can be mixed in any desired ratio without the limiting oxygen concentration being exceeded. Only when the air feed rate exceeds the first third of its intended maximum value is the monitoring of the operating point activated by the safety programmable logic control (SPLC). It is true that EP-B 1180508 describes an alternative method for starting up a reactor with a high level of safety. However, this assumes an exact determination of the relevant gas streams in the lower measuring range of the measuring apparatuses, something which as a rule does not occur owing to the basic physical principles on which the quantitative measurements are based. In contrast, shutting down the heterogeneously catalyzed gas-phase partial oxidation is less critical if the air feed is closed first.

Other heterogeneously catalyzed partial oxidation, for example the heterogeneously catalyzed partial oxidation of isobutene to methacrolein and/or methacrylic acid (one-stage, or the first stage of a two-stage process), a one-stage heterogeneously catalyzed partial oxidation of propane to acrolein and/or acrylic acid, a one-stage heterogeneously catalyzed partial oxidation of isobutane to methacrolein and/or methacrylic acid, a one-stage heterogeneously catalyzed partial oxidation of alkylene to alkylene oxide (e.g. ethylene oxide or propylene oxide), a one-stage heterogeneously catalyzed partial oxidation of acrolein to acrylic acid, etc., can also be carried out in a completely corresponding manner to the abovementioned heterogeneously catalyzed partial oxidation of propylene to acrolein and/or acrylic acid. This applies particularly when the total amount of inert diluent gas concomitantly used comprises ≧90% by volume or ≧95% by volume of nonflammable inert diluent gases.

However, it can also be used in an outstanding manner when, as in the processes described in DE-A 10131297, DE-A 10219685, DE-A 10219686 and WO 01/96270, the compound to be partially oxidized is an alkylene and a flammable inert diluent gas, i.e. alkane homologous to the alkylene (e.g. propane in the case of propylene, isobutane in the case of isobutene) is also concomitantly used as inert diluent gas in addition to nonflammable gases.

Since the alkylene/$O_2$—$N_2$ or homologous alkane/$O_2$—$N_2$ explosion diagrams scarcely differ from one another, one of the two can be deposited as a characteristic explosion diagram in the computer. The novel process is additionally simplified when the recycle gas is recycled into the catalytic dehydrogenation upstream of the partial oxidation so that $N_2$ and the homologous alkane are substantially the only inert diluent gases in the partial oxidation.

However, the novel process can also be used when only flammable inert diluent gases are used as inert diluent gas.

It may be necessary for this purpose to extend the number of component axes in the explosion diagram to more than two, as shown in principle in the figure in DE-A 19902562. In the case of ammoxidations, the ammonia is included in the explosion diagram.

The novel process can be applied to the second stage of a two-stage heterogeneously catalyzed gas-phase oxidation of propene to acrylic acid or of isobutene to methacrylic acid in a tube-bundle reactor even when this second stage directly contains, as feed gas mixture, the product gas mixture of the first stage and air (secondary air) added to this (in a mixer). The operating point of the feed gas mixture of the second stage can then be determined in a simple manner from the operating point, determinable as described, of the feed gas mixture for the first stage and its amount and the amount of secondary air. This is possible because the catalyst properties under the reaction conditions chosen for the first stage are known (propylene conversion usually $\geq 90$ or $\geq 95$ mol %, selectivity of the acrolein formation $\geq 90$ mol %, remaining byproduct selectivity substantially carbon oxide and steam formation), so that the composition of the product gas mixture leaving the first stage can be calculated from the feed gas mixture for the first stage without additional necessity of measurements.

In the simplest case, the acrolein/$O_2$—$N_2$ diagram is deposited as a characteristic explosion diagram.

The presence of CO therein results in a shift of the explosion limit curve to the right. Regarding pressure and temperature, a procedure analogous to that for the first stage can be adopted. Here, the reaction temperatures are from 230 to 300° C., depending on the catalyst used. The inlet pressure is as a rule from 1 to 5 bar also in the second stage.

Figure 4:
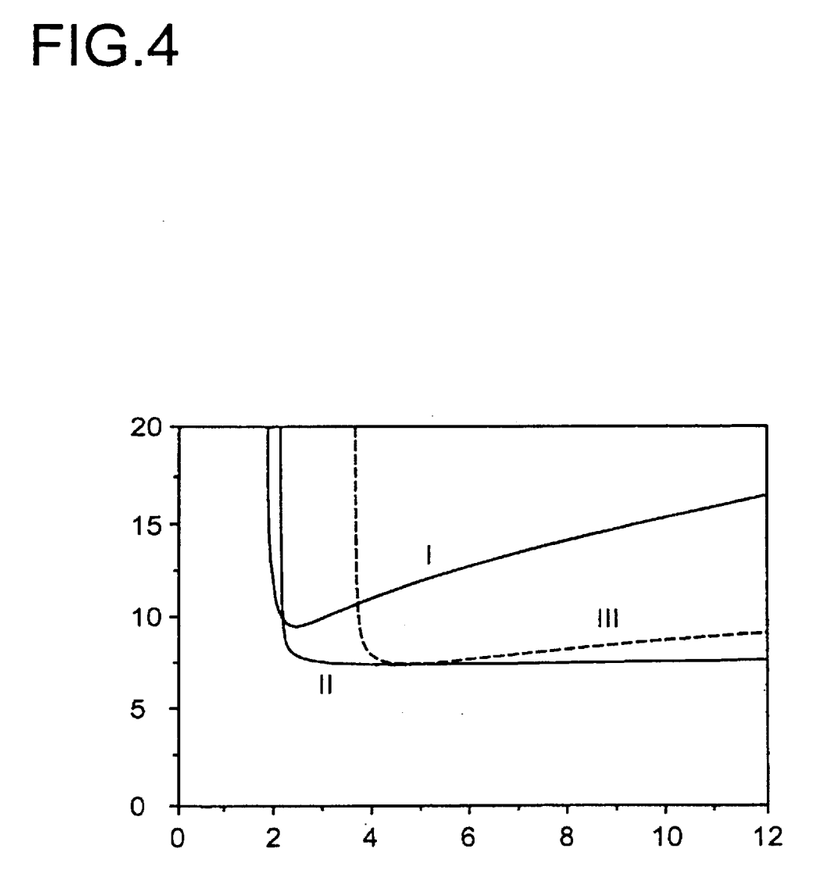
FIG. 4 shows an explosion diagram for a propylene/$O_2$-$N_2$, and acrolein CO/$O_2$-$N_2$ systems.

FIG. 4 shows typical explosion diagrams for the systems propylene/$O_2$—$N_2$ (I), acrolein/$O_2$—$N_2$ (II) and acrolein, CO/$O_2$—$N_2$ (III) (the CO concentration was kept constant at 1.6% by volume there).

As an alternative to the novel process, it has also been proposed to use only a maximum amount of secondary air or a maximum ratio of the amounts of secondary air/primary air (air fed to the first stage) or a maximum oxygen concentration in the product gas mixture of the second stage as a cut-out variable for the second stage apart from the control system for the first stage. Particularly the last cut-out mechanism, however, is unsatisfactory since it reacts only with a time lag, i.e. when the incorrect feed leaves the second stage. The cut-out mechanism acts here primarily on the secondary air feed.

Finally, it should be noted that a cut-out scenario for the second stage is also conceivable on the basis of the following two cut-out variables: maximum ratio of amount of secondary air fed to the second stage to amount of crude propylene fed to the first stage and maximum propylene concentration in the product gas mixture of the second stage.

Finally, it should also be mentioned that heterogeneously catalyzed propylene partial oxidations to acrolein and/or acrylic acid can be carried out without problems by the novel process, the feed gas mixture of said partial oxidations containing up to 10% by volume or more of propylene at a molar $O_2$/propylene ratio of >1.

The loading of the catalysts with feed gas mixture may be chosen as in DE-A 19910508 or DE-A 19910506. The working-up for recycle gas recovery can be effected as in WO 97/48669.

In this document, continuous operation means that starting gas mixture is fed continuously to the reactor over a relatively long period, as a rule at least a few days, without interruption and product gas mixture is removed continuously.

We claim:

1. A process for the safe operation of a continuously operated heterogeneously catalyzed gas-phase partial oxidation of at least one organic compound in an oxidation reactor whose feed gas mixture comprises, in addition to the at least one organic compound to be partially oxidized and molecular oxygen as an oxidizing agent, at least one diluent gas substantially inert under the conditions of the heterogeneously catalyzed gas-phase partial oxidation, in which a cut-out mechanism is used during said gas phase partial oxidation to prevent the oxidation reactor from being fed with a feed gas mixture whose composition is an explosive one, wherein the cut-out mechanism is designed as follows:

a) an explosion diagram which is characteristic of the feed gas mixture and in which a distinction is made between explosive and nonexplosive compositions as a function of the composition of the feed gas mixture is deposited in a computer;

b) a data record is established by determination with respect to the amount and, if required, composition of the gas streams fed to the reactor for producing the feed gas mixture, and is transmitted to the computer;

c) the computer calculates an actual operating point of the feed gas mixture in the explosion diagram from the data record obtained under b);

d) if the distance from the operating point to the nearest explosion limit is below a predetermined minimum value, the feed of gas streams to the reactor is automatically stopped.

2. A process as claimed in claim 1, wherein the at least one organic compound is propylene, isobutene, ethylene, propane, isobutane, acrolein or methacrolein.

3. A process as claimed in claim 1, wherein the oxygen content of the feed gas mixture is above the limiting oxygen concentration of the feed gas mixture.

4. A process as claimed in claim 3, wherein the oxygen content of the feed gas mixture is $\geq 0.5\%$ by volume above the limiting oxygen concentration of the feed gas mixture.

5. A process as claimed in claim 1, wherein the oxygen source used is air.

6. A process as claimed in claim 1, wherein the inert diluent gas comprises $\geq 90\%$ by volume of nonflammable components.

7. A process as claimed in claim 1, wherein the inert diluent gas comprises $\geq 95\%$ by volume of nonflammable components.

8. A process as claimed in claim 1, wherein the inert diluent gas comprises $\geq 90\%$ by volume of $N_2$, $H_2O$ and/or $CO_2$.

9. A process as claimed in claim 1, wherein the inert diluent gas comprises $\geq 95\%$ by volume of $N_2$, $H_2O$ and/or $CO_2$.

10. A process as claimed in claim 1, wherein recycle gas is used as a source of the inert diluent gas.

11. A process as claimed in claim 1, wherein Venturi tubes are used for determining the amounts of the gas streams fed to the reactor.

12. A process as claimed in claim 1, wherein the oxygen source used is air and the air feed to the reactor is stopped when the distance from the operating point to the nearest explosion limit is below the predetermined minimum value.

13. A process as claimed in claim 1, wherein the at least one organic compound is propylene and the characteristic explosion diagram is the explosion diagram of the mixture propylene/$O_2$—$N_2$.

14. A process as claimed in claim 1, wherein the minimum value is calculated from a statistical error evaluation of the measured quantities required for calculating the operating point.

15. A process as claimed in claim 1 wherein the computer is a safety programmable logic controller (SPLC).

16. A computer-based method for a continuous, heterogeneously catalyzed gas-phase partial oxidation of at least one organic compound in an oxidation reactor that includes feeding a gas mixture comprising at least one organic compound, molecular oxygen, and at least one diluent gas substantially inert under the conditions of the heterogeneously catalyzed gas-phase oxidation to an oxidation reactor, and preventing the feeding of an explosive gas mixture to the oxidation reactor with a cut-out mechanism, comprising:

inputting an explosion diagram which is characteristic of a feed gas mixture and having at least one non-explosive region and at least one explosive region, and one or more safety regions separating the explosive and non-explosive regions, and wherein the regions are defined as a function of the composition of the feed gas mixture;

inputting the amount and, if required, the composition of the gas streams fed to the oxidation reactor;

calculating in the explosion diagram an operating point of the feed gas mixture resulting from the gas streams fed to the oxidation reactor;

considering the position of the operating point within the inputted explosion diagram to determine if the operating point is in a non-explosive or explosive region of the explosion diagram;

stopping the feed of gas streams to the oxidation reactor if the operating point is in an explosive region or in a safety region of the explosion diagrams, wherein the cut-out mechanism is used during said gas phase partial oxidation.

17. The process as claimed in claim 16, wherein the heterogeneously catalyzed gas-phase partial oxidation is carried out in a non-explosive region of the explosion diagram and the gas feed mixture has an oxygen amount greater than the minimum amount of oxygen in any explosive region of the explosion diagram.

18. The process as claim 1, wherein the heterogeneously catalyzed gas-phase partial oxidation is carried out in a non-explosive region of the explosion diagram and the gas feed mixture has an oxygen amount greater than the minimum amount of oxygen in any explosive region of the explosion diagram.

* * * * *